United States Patent [19]
Kercher

[11] Patent Number: 4,629,562
[45] Date of Patent: Dec. 16, 1986

[54] PULSE DAMPENER
[75] Inventor: Paul W. Kercher, Furnace, Pa.
[73] Assignee: Scientific Systems, Inc., State College, Pa.
[21] Appl. No.: 762,943
[22] Filed: Aug. 6, 1985
[51] Int. Cl.⁴ .................. B01D 15/08; F16L 55/04
[52] U.S. Cl. .................. 210/198.2; 210/101; 73/61.1 C; 138/30; 417/540
[58] Field of Search ............ 210/656, 657, 658, 659, 210/198.2, 198.3, 101; 138/30; 417/540; 73/61.1 C

[56] References Cited
U.S. PATENT DOCUMENTS

| 2,852,033 | 9/1958 | Orser | 138/30 |
| 2,904,077 | 9/1959 | Trumper | 138/30 |
| 3,442,293 | 5/1969 | Erdmann | 138/30 |
| 4,088,154 | 5/1978 | Patton | 138/30 |
| 4,222,414 | 9/1980 | Achener | 138/30 |
| 4,427,029 | 1/1984 | Charney | 210/198.2 |
| 4,548,713 | 10/1985 | Schmid | 210/198.2 |
| 4,552,182 | 11/1985 | Graham | 138/30 |

Primary Examiner—Ernest G. Therkorn
Attorney, Agent, or Firm—Eric P. Schellin

[57] ABSTRACT

A pulse dampener for inclusion into a liquid chromatography system comprising a body defining a cylindrical cavity which is enclosed by a closure member. A chemically inert diaphram extends across the cavity and further encloses a unitized plug. The unitized plug is provided with at least two portions, each having different compressibility characteristics. The closure member is provided with inlet and outlet ports, and a central thinned section on which is mounted a strain gauge. The strain gauge is used to measure liquid pressure in the dampener.

18 Claims, 3 Drawing Figures

PULSE DAMPENER

BACKGROUND OF THE INVENTION

1. Field of the Invention

The invention is directed to a pulse dampener for high pressure liquid chromatography comprising a unitized plug having two portions, each portion having different compressibility characteristics.

2. Description of the Prior Art

In high pressure liquid chromatography a chromatographic column is connected by a suitable conduit to a reciprocating type pump that operates to transmit a liquid vehicle from a supply reservoir. The liquid vehicle is transmitted through a pulse dampener and then transmitted to an injection valve wherein a liquid sample is entrained in the liquid vehicle. The liquid vehicle and sample are then transported through the chromatographic column for determination of the constituents of the sample. The liquid vehicle is usually a chemical solvent which is non-reactive with the sample, and neither the sample or the solvent are reactive with the material from which the column is packed.

In chromatographic systems the solvent flow paths should have minimal internal volume and be well swept to afford continuous movement of the liquid solvent and sample through the system. This is important in solvent changeover and gradient chromatography techniques. If excessive internal volume exists it tends to cause mixing which is detrimental to efficient solvent changeover and causes loss of predictable time-based solvent proportions in gradient work.

Various types of pulse dampeners have been developed for various purposes. U.S. Pat. No. 3,333,604, discloses a pulse dampener for use in a high pressure car washing equipment. Other examples of fluidic pulse dampeners are disclosed in U.S. Pat. Nos. 2,216,374, 2,354,201, 2,808,070, 3,851,661 and 4,452,069.

U.S. Pat. No. 2,883,180, discloses a hydraulic accumulator formed of a rubber spring. In selected embodiments the rubber springs are provided with a thick diaphram that maybe formed of synthetic rubber or a rubber like material.

Pulse dampeners have also been developed for chromatography systems, as disclosed in U.S. Pat. Nos. 4,163,461 and 4,186,776. Each of these dampeners is provided with a bulbous shaped cavity having a flexible diaphram arranged across the cavity. One side of the diaphram is exposed to the fluid pumped by the reciprocating pump while the other side is exposed to a compressible fluid.

In U.S. Pat. No. 3,984,315, a pulse dampener has been prosed wherein a flexible diaphram extends across a cavity. One side of the diaphram is exposed to the fluid from the reciprocating pump and the other side is provided with a coil spring that is positioned to resist flexing of the diaphram.

In high pressure liquid chromatography dampeners maybe formed of a plastic spool having an axial bore to receive liquid from the pump. The spool is preferably made of polytetrafluoro-ethylene which is chemically inert to the fluids typically used in liquid chromatography. The spool is encased in a stainless steel cylindrical housing which is filled with a compressible liquid. Such a dampener is disclosed in U.S. Pat. No. 4,222,414. In U.S. Pat. No. 4,024,061, a pulse dampener has been proposed that comprises a block of solid material, such a polytetrafluoro-ethylene, which occupies 99% of the volume of a cavity. See also U.S. Pat. No. 4,045,343.

SUMMARY OF THE INVENTION

The present invention is directed to a high pressure liquid chromatography pulse dampener comprising a solid utilized plug that is disposed in a cavity. A diaphram overlies the unitized plug and is exposed to the liquid through inlet and outlet ports in a closure member enclosing the cavity. The unitized plug has two portions, each portion having a different compressibility characteristic. This enables the dampener to have a wider dynamic range and allows the dampener to be customized to match a particular dampening problem. The closure member is provided with a thinned section having a strain gauge to monitor the pressure in the cavity.

DETAILED DESCRIPTION

The present invention is directed to a pulse dampener for liquid chromatography. A similar dampener is disclosed in U.S. Pat. No. 4,427,029, which was patented by the applicant, and is incorporated herein by reference.

Figure 1:
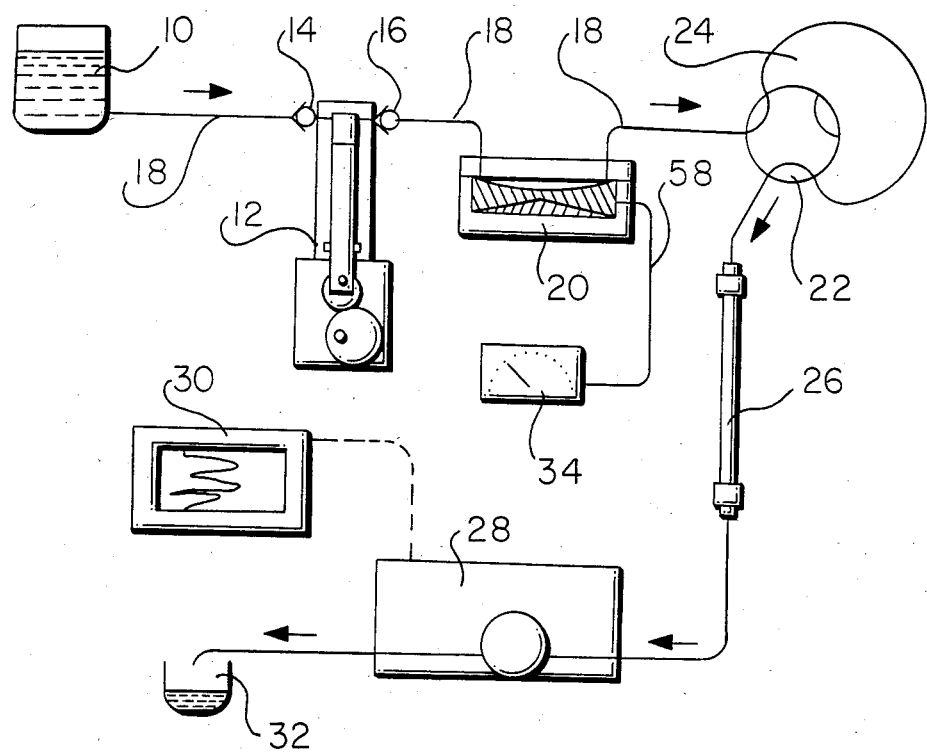
FIG. 1 is a diagrammatic view of a chromatography system which includes a pulse dampener of the present invention.

For the purposes a providing a relatively simple presentation of a chromatography system in which the pulse dampener of the present invention is included your attention is directed to FIG. 1. In practicing high pressure liquid chromatography, a mobile phase or liquid vehicle is provided in reservoir 10 which is in communication with reciprocating pump 12 having check valves 14 and 16. Conduit 18 directs the liquid from the reservoir through the pump to pulse dampener 20 of the present invention. The conduit then communicates with injection valve 22 that is couples to sample storage supply 24 which contains the material to be analyzed. The sample material is sequentially injected into one end of chromatography column 26 which is packed with material, as dictated by chromatography practice, for separating the various components of the sample material. A number of columns may be connected in series for analyzing relatively complex sample materials.

In operation the liquid vehicle of chromatography systems must not react chemically with the sample material, and correspondingly the sample material and the liquid vehicle should not react with the material packed in the column. In modern sophisticated chromatography systems detector 28 may also be provided so that the components of the sample material maybe automatically recorded for print out on mechanism 30. After analysis the sample material may be segregated and/or discharged into waste means 32. In addition the pulse dampener is coupled to pressure indicator 34 for indicating the fluid pressure in the dampener.

Figure 2:
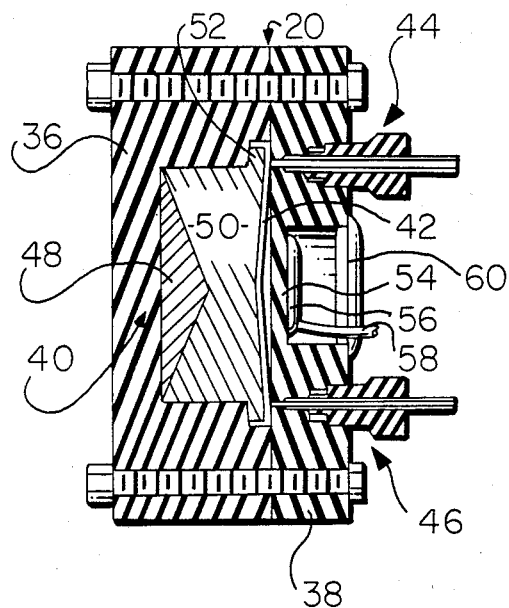
FIG. 2 is a cross sectional view of the pulse dampener of the present invention.
Figure 3:
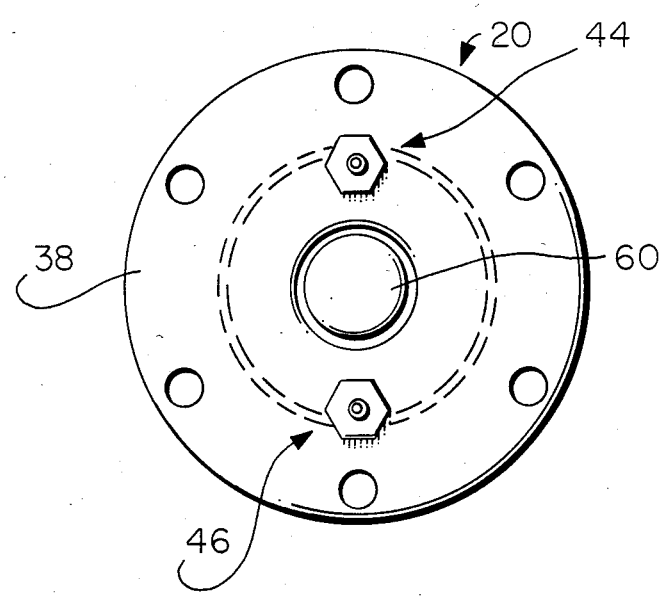
FIG. 3 is a top view of the pulse dampener of the present invention.

The details of the present pulse dampener are best illustrated in FIGS. 2 and 3. Pulse dampener 20 comprises body 36 having a cylindrical cavity which is enclosed by closure member 38. Cylindrical unitized plug 40 is positioned in the cavity and sealed off from the closure member by chemically inert diaphram 42. The diaphram may be formed of FEP, TFE, or Kalrex. The closure member is provided with inlet and outlet ports 44 and 46, respectively, through which the liquid vehicle from the reciprocating pump passes.

The unitized plug has two portions 48 and 50, each having different compressibility characteristics. First portion 48 is conically shaped and integrally fitted into second portion 50 which is provided with a surface for receiving the conical first portion. The second portion is also provided with a concave outer face adjacent to diaphram 42 which allows for expansion due to temperature rise while also aiding in sweeping the liquid containing area when liquid is pumped through the dampener. Both portions extend across the entire cavity parallel to the diaphram. The outer periphery of the unitized plug is provided with rim 52 that forms a sealing protuberance for the diaphram with the closure member.

The unitized plug can be made of silicon rubber and or other rubber materials with varying compressibility characteristics. By adjusting the materials, and the geometry of the different compressibility portions of the unitized plug, the dampener can be specifically adapted for different chromatography problems.

The closure member of the dampener is provided with thinned section 54 having strain gauge 56. The strain gauge is provided with electrical wires 58 which are coupled to indicator 34 for measuring the liquid pressure in the dampener. The strain gauge is protected by plastic cover 60. In operation the thinned section acts as a diaphram which deflects in response to the liquid pressure in the dampener, and these deflections are picked up by the strain gauge and transmitted through electrical wires 58 to pressure indicator 34 which provides a corresponding liquid pressure.

The above described dampener is not limited to any particular geometric configuration but maybe configured in any particular way that is appropriate for the chromatographic use to which it will be put. As such the pulse dampener of the present invention should not be limited to the above-described embodiment but should be solely limited by the claims that follow:

I claim:

1. A pulse dampener for use with a reciprocating pump in a chromatography system to minimize the effects of the pulsations of the liquid delivered to the chromatography column, said dampener comprising:
   inlet and outlet ports for a liquid vehicle;
   a body defining a cavity;
   a closure member extending across the cavity enclosing the cavity; and
   a unitized plug positioned within the cavity of said body, the unitized plug having at least two portions having different compressibility characteristics.

2. A pulse dampener as defined in claim 1 wherein said closure member is provided with inlet and outlet ports for a liquid vehicle.

3. A pulse dampener as defined by claim 2 further comprising a diaphram that extends across the cavity sealing the utilized plug from the inlet and outlet ports.

4. A pulse dampener as defined by claim 3 wherein each portion of the unitized plug extends across the entire cavity parallel to the diaphram.

5. A pulse dampener as defined by claim 4 wherein the cavity is cylindrical and the unitized plug is cylindrical having a circular periphery.

6. A pulse dampener as defined by clalim 5 wherein one portion of the unitized plug is conical and the other portion has a receiving surface for the conical portion.

7. A pulse dampener as defined by claim 6 wherein the unitized plug has a rim about its periphery forming a sealing protuberance for the diaphram.

8. A pulse dampener as defined by claim 7 wherein the unitized plug has a concave surface adjacent to the diaphram.

9. A pulse dampener as defined by claim 8 wherein the closure member is circular and provided with a central thinned section on which a strain gauge is mounted for sensing liquid pressure within said dampener.

10. An improved liquid chromatography system wherein a liquid vehicle from a supply reservoir is directed through a reciprocating pump to an injection valve which is coupled to sample material for directing the liquid vehicle and the sample material to a chromatography column, the improvement comprising:
    a pulse dampener positioned between the reciprocating pump and the injection valve, said dampener comprising inlet and outlet ports for a liquid vehicle, a body defining a cavity which is enclosed by a closure member, a unitized plug is positioned within the cavity and has at least two portions each having different compressibility characteristics.

11. A chromatography system as defined by claim 10 wherein said closure member is provided with inlet and outlet ports for a liquid vehicle.

12. A chromatography system as defined by claim 11 further comprising a diaphram that extends across the cavity sealing the unitized plug from the inlet and outlet ports.

13. A chromatography system as defined by claim 12 wherein each portion of the unitized plug extends across the entire cavity parallel to the diaphram.

14. A chromatography system as defined by claim 13 wherein the cavity is cylindrical and the unitized plug is cylindrical having a circular periphery.

15. A chromatography system as defined by claim 14 wherein one portion of the unitized plug is conical and the other portion has a receiving surface for the conical portion.

16. A chromatography system as defined by claim 15 wherein the unitized plug has a rim about its periphery forming a sealing protuberance for the diaphram.

17. A chromatography system as defined by claim 16 wherein the unitized plug has a concave surface adjacent to the diaphram.

18. A chromatography system as defined by claim 17 wherein the closure member is circular and provided with a central thinned section on which a strain gauge is mounted for sensing liquid pressure within said dampener.

* * * * *